US006258748B1

(12) United States Patent
Hamley

(10) Patent No.: US 6,258,748 B1
(45) Date of Patent: *Jul. 10, 2001

(54) FLORAL PRESERVATIVE AND AROMATHERAPY APPARATUS AND METHOD

(76) Inventor: Robert J. Hamley, 663 Main St., Hunter, NY (US) 12442

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/428,205
(22) Filed: Oct. 27, 1999
(51) Int. Cl.$^7$ .................................................. A01N 3/02
(52) U.S. Cl. ............................................................ 504/114
(58) Field of Search ............................................. 504/114

(56) References Cited

U.S. PATENT DOCUMENTS

| | | | | |
|---|---|---|---|---|
| 116,375 | * | 6/1871 | Vining | 504/114 |
| 1,779,299 | * | 10/1930 | Valentine | 504/114 |
| 3,791,839 | | 2/1974 | Cushman et al. | 106/268 |
| 3,929,448 | * | 12/1975 | Brantley | 71/86 |
| 4,348,424 | | 9/1982 | Consalazio et al. | 427/4 |
| 4,885,175 | | 12/1989 | Zibell | 426/5 |
| 5,723,407 | * | 3/1998 | Midou et al. | 504/115 |
| 5,834,074 | | 11/1989 | Mikkola | 504/114 |

FOREIGN PATENT DOCUMENTS 2 189 676   11/1987   (GB) .

OTHER PUBLICATIONS

Creekmore, Betsey B. Making Gifts from Oddments & Outdoor Materials. Hearthside Pr.: NY. pp. 167–169.*
Databasde WPI, Section Ch. Week 199431, Derwent Publications Ltd., London, GB; Class E19, AN 1994–252656, XP002161255 & JP 06 183903 (Hyponex Japan KK), Jul. 5, 1994.
Database WPI, Sect. Ch, Week 199624, Derwent Publications Ltd., London, GB; Class A97, AN 1996–235893, XP002161256 & JP 08 092003 (Toppon Printing Co. Ltd.), Apr. 9, 1996.
Database WPI, Section Ch, Week 199431, Derwent Publications Ltd., London, GB; Class E19, AN 1994–252656, XP002161255 & JP 06 183903 (Hyponex Japan KK), Jul. 5, 1994.
Database WPI, Section Ch, Week 199624, Derwent Publications Ltd., London, GB; Class A97, AN 1996–235893, XP002161256 & JP 08 092003 (Toppon Printing Co. Ltd.), Apr. 9, 1996.

* cited by examiner

Primary Examiner—S. Mark Clardy
(74) Attorney, Agent, or Firm—Jay R. Yablon

(57) ABSTRACT

To preserve flowers and provide aromatherapy, low temperature paraffin is heated to a liquid state of approximately 130 degrees Fahrenheit. A floral nutrient and preservative such as sugar is then added to the low temperature paraffin. Optionally, scents and/or color dyes are also added. The heads of flowers to be preserved are then dipped in this paraffin mixture for one to three seconds and thereafter allowed to dry. The flower can then be used immediately, or optionally hung upside down for one to three weeks prior to use to further improve shelf life.

24 Claims, 1 Drawing Sheet

FLORAL PRESERVATIVE AND AROMATHERAPY APPARATUS AND METHOD

FIELD OF THE INVENTION

This invention relates to the field of floral preservatives, and specifically, to a device and method used to preserve cut flowers well beyond their ordinary shelf life.

BACKGROUND OF THE INVENTION

Flowers have long been a special gift for birthdays, anniversaries, weddings, and many other special occasions. However, the gift of flowers only lasts for a short time. Within a few short days or weeks, cut flowers wilt and die unless they have been properly preserved.

Over time, various approaches to preserving flowers have been developed. These include freeze drying, hang drying, use of silica gels and sand mixtures, and spraying with the various compounds such as polyurethane, hairspray, and shellac. However, none of these approaches is fully satisfactory in terms of the shelf life achieved, the ability to achieve a lasting, pleasant aroma, and/or providing suitable coloration.

Additionally, desired scents and colorations, if any, are frequently introduced after the flower has already been preserved, rather than during the preservation process itself, which makes these susceptible to wearing off over time.

OBJECTS OF THE INVENTION

It is desirable, therefore, to provide an improved device and method for preserving flowers which increases their shelf life substantially.

It is further desirable to integrate such an improved device and method for preserving flowers with an improved device and method to provide a lasting, pleasant aroma, and/or the ability to provide suitable coloration to the preserved flowers.

SUMMARY OF THE INVENTION

Low temperature paraffin is heated to a liquid state of approximately 130 degrees Fahrenheit. A floral nutrient and preservative such as sugar is then added to the low temperature paraffin. Optionally, scents and/or color dyes are also added. The heads of the flowers to be preserved are then dipped in this paraffin mixture for one to three seconds and thereafter allowed to dry. The flower can then be used immediately, or optionally hung upside down for one to three weeks prior to use to further improve shelf life.

BRIEF DESCRIPTION OF THE DRAWING

The features of the invention believed to be novel are set forth in the appended claims. The invention, however, together with further objects and advantages thereof, may best be understood by reference to the following description taken in conjunction with the accompanying drawing in which:

DETAILED DESCRIPTION OF THE INVENTION

Figure 1:
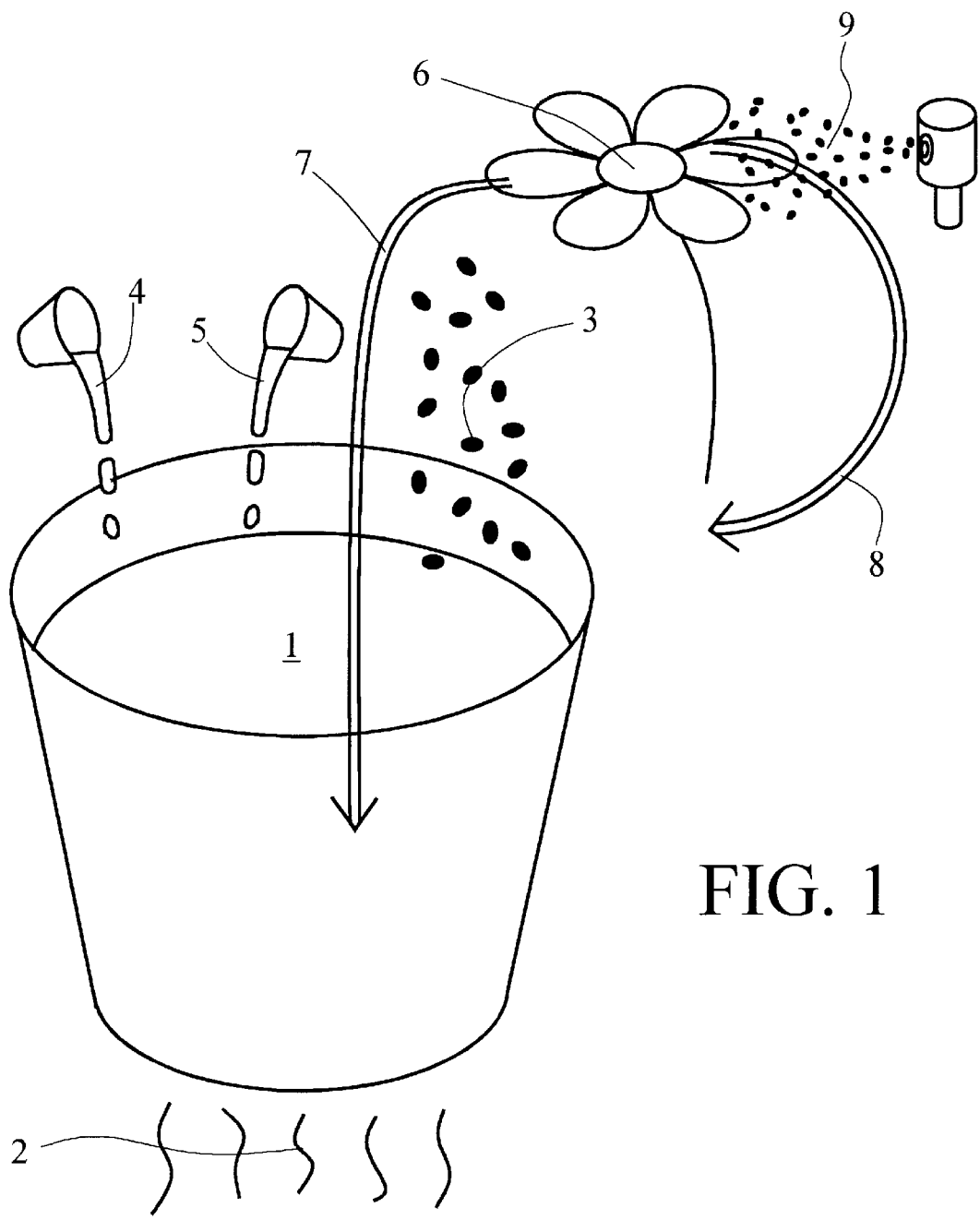
FIG. 1 is a schematic view illustrating the apparatus and method through which the paraffin mix used to preserve flowers is prepared and used in the preferred embodiment of the invention.

Low temperature paraffin 1 is first heated 2 to a liquid state of approximately 130 degrees Fahrenheit. In a preferred embodiment, low temperature paraffin 1 is a member of the petroleum hydrocarbon family, and is preferably a petroleum paraffin wax. It is preferred that low temperature paraffin 1 be highly refined so as to comprise long chain saturated hydrocarbon molecules.

Next, a floral nutrient and preservative 3 is mixed into low temperature paraffin 1. In a preferred embodiment, floral nutrient and preservative 3 comprises sugar, preferably white granulated or liquid sugar. Approximately one pinch of floral nutrient and preservative 2 is added for each pound of low-temperature paraffin 1. In alternative embodiment of the invention, floral nutrient and preservative 3 may comprise, alternatively or in addition to sugar, one or more of honey, saccharin, aspartame, or any other known sweetener.

Next, for each pound of low-temperature paraffin 1, approximately ½ ounce of scent 4 is added. Scent 4 can be a floral or a non-floral scent, and is generally in a liquid form but may also be in a powder of other solid form as well within the scope of this disclosure and its associated claims. Scent 4 may comprise, but is not limited to, one or more of: jasmine, rose, lavender, petitgrain, patchouli, juniper, ginger, orange blossom, tangerine, rosemary, peppermint, peach blossom, eucalyptus, lemon, balsam fir, bergamot, ylang, neroli, sandalwood, chamomile, geranium, musk, frankincense, cedar, plum, mandarin, pine, tea tree, clary sage, vetiver, cypress, coriander, lemon, grapefruit, bergamot, cordamom, basil, lilac, everlasting, lily, lily of the valley, and any and all other known scents.

Optionally, if coloration is desired, approximately ¹⁄₂₄ gram of a colored dye 5 for whatever color is desired is then added, for each pound of low-temperature paraffin 1. Dye 5 is also typically a liquid, but can also be a powder or similar solid formulations as well within the scope of this disclosure and its associated claims.

Finally, the flower 6 head only, is dipped 7 into the above paraffin mixture comprising low-temperature paraffin 1 and any or all of floral nutrient and preservative 3, scent 4, and dye 5, for a predetermined dip time of approximately one to three seconds. Then, flower 6 is used for decorative purposes and/or for aromatherapy, as desired. A single, short dip 7 such as described above coats the flower lightly with the paraffin mix and keeps the flower looking more natural and alive. Longer, and/or multiple dips, would cause the flower to appear heavy and waxy, and would diminish shelf life.

Optionally, prior to use, to bring about an even longer shelf life, flower 6 may be hung upside down 8 for a predetermined hang time of approximately one to three weeks, or until the stem becomes hard like a stick. This strengthens the flower stem and enables it to better support the weight of the paraffin mixture on the flower 6 head.

Floral nutrient and preservative 3 is particularly important, since it adds a great deal of shelf life to preserved flower 6 over what is achieved by dipping in low temperature paraffin 1 alone. In particular, formaldehyde contained within sugar and similar embodiments of floral nutrient and preservative 3 is released from the paraffin mix over time, so that floral nutrient and preservative 3 not only feeds flower 6, but also acts to preserve/mummify it. From a functional standpoint, this means that any nutrient which feeds flower 6 over time and also releases formaldehyde or a similar preservative compound over time is suitable for use as floral nutrient and preservative 3.

Scent 4 allows flower 6 to emit a pleasing aroma long after flower 6 has been preserved, and enables flower 6 to be used for aromatherapy and related purposes.

It is also possible, for aromatherapy, maintain the paraffin mix comprising low temperature paraffin 1 and scent 4 in a heated, liquid state, whether or not a flower is dipped into it. Aroma from this mix then wafts into the surrounding environment, again, providing a pleasing aroma.

After flower 6 has been dipped 7, dried, and optionally hung 8, flower 6 may optionally be sprayed with a floral spray paint 9. This adds more shine to flower 6, and keeps the color more vibrant and realistic-looking over time.

It is to be understood that for commercial purposes, it may be desirable to prepare the entire paraffin mixture in a mass-production setting, cool the paraffin mixture into a portable solid, and then distribute this cooled, solid paraffin mixture to the end user in tubs or similar containers. These tubs, and the solid paraffin mixture they contain, would then be slowly heated by the end user to approximately 130 degrees and liquefied as noted above. This slow heating can utilize any of the means known in the art for such a purpose. For example, it can be heated in a double-boiler, where the temperature of the heated water is maintained below about 160 degrees Fahrenheit; or in a crock pot with a suitable controlled temperature. The low (130 degree) temperature (and quick dip) is important for a number of reasons, including that this minimizes possible adverse impacts of heat on the flower itself. Flowers 6 are then dipped 7 into this heated liquid paraffin mixture as outlined above.

It is to be understood that the invention disclosed and claimed herein includes all of: the paraffin mixture disclosed herein (flower preservative product/composition of matter); the method by which this paraffin mixture is produced (method of manufacturing flower preservative product); the method by which flowers are preserved using this paraffin mixture (flower preservative process); and preserved flowers which are themselves produced by this flower preserving process (preserved flower products by flower preservative process).

While only certain preferred features of the invention have been illustrated and described, many modifications and changes will occur to those skilled in the art. It is, therefore, to be understood that the appended claims are intended to cover all such modifications and changes as fall within the true spirit of the invention.

I claim:

1. A floral preservative, comprising:
   low-temperature paraffin; and
   a floral nutrient and preservative consisting only of at least one saccharide, mixed into said paraffin.

2. The floral preservative of claim 1, further comprising:
   at least one scent mixed into said paraffin.

3. The floral preservative of claim 1, further comprising:
   at least one colored dye mixed into said paraffin.

4. The floral preservative of claim 2, further comprising:
   at least one colored dye mixed into said paraffin.

5. A method of manufacturing a floral preservative, comprising the steps of:
   heating low temperature paraffin to a liquid state; and
   mixing a floral nutrient and preservative consisting only of at least one saccharide, into said paraffin.

6. The manufacturing method of claim 5, further comprising the steps of:
   mixing at least one scent into said paraffin.

7. The manufacturing method of claim 5, further comprising the steps of:
   mixing at least one colored dye into said paraffin.

8. The manufacturing method of claim 6, further comprising the steps of:
   mixing at least one colored dye into said paraffin.

9. The manufacturing method of claim 5, further comprising the steps of:
   cooling paraffin to a solid state after mixing said floral nutrient and preservative into said paraffin.

10. The manufacturing method of claim 6, further comprising the steps of:
    cooling said paraffin mixture to a solid state after mixing said floral nutrient and preservative, and said scent, into said paraffin.

11. The manufacturing method of claim 7, further comprising the steps of:
    cooling said paraffin mixture to a solid state after mixing said floral nutrient and preservative, and said colored dye, into said paraffin.

12. The manufacturing method of claim 8, further comprising the steps of:
    cooling said paraffin mixture to a solid state after mixing said floral nutrient and preservative, said scent, and said colored dye, into said paraffin.

13. A method of preserving flowers, comprising the steps of:
    dipping at least a head of a flower into a floral preservative heated into a liquid state, said floral preservative comprising:
    low-temperature paraffin; and
    a floral nutrient and preservative consisting only of at least one saccharide, mixed into said paraffin.

14. The method of claim 13, said floral preservative further comprising:
    at least one scent mixed into said paraffin.

15. The method of claim 13, said floral preservative further comprising:
    at least one colored dye mixed into said paraffin.

16. The method of claim 14, said floral preservative further comprising:
    at least one colored dye mixed into said paraffin.

17. The method of claim 13, comprising the further step of:
    hanging said flower upside down for a predetermined hang time subsequent to said dipping, thereby hardening a stem of said flower.

18. The method of claim 13, comprising the further step of:
    spraying said flower with a floral spray paint.

19. A preserved flower produced by a method of producing preserved flowers, said method comprising the steps of:
    dipping a head of said flower into a floral preservative, said floral preservative comprising:
    low-temperature paraffin; and
    a floral nutrient and preservative consisting only of at least one saccharide, mixed into said paraffin.

20. The preserved flower of claim 19, said floral preservative further comprising:
    at least one scent mixed into said paraffin.

21. The preserved flower of claim 19, said floral preservative further comprising:
    at least one colored dye mixed into said paraffin.

22. The preserved flower of claim 20, said floral preservative further comprising:
    at least one colored dye mixed into said paraffin.

23. The preserved flower of claim 19, said method of producing preserved flowers comprising the further step of:
    hanging said flower upside down for a predetermined hang time subsequent to said dipping, thereby hardening a stem of said flower.

24. The preserved flower of claim 19, said method of producing said preserved flowers comprising the further step of:
    spraying said flower with a floral spray paint.

* * * * *